US010849627B2

(12) United States Patent
Saum et al.

(10) Patent No.: US 10,849,627 B2
(45) Date of Patent: Dec. 1, 2020

(54) ARTERIOVENOUS FISTULA IMPLANT EFFECTIVE FOR INDUCING LAMINAR BLOOD FLOW

(71) Applicant: UNIVERSITY OF CINCINNATI, Cincinnati, OH (US)

(72) Inventors: Keith Louis Saum, Cincinnati, OH (US); Prabir Roy-Chaudhury, Cincinnati, OH (US); Begona Campos-Naciff, Cincinnati, OH (US); Diego Celdran-Bonafonte, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 344 days.

(21) Appl. No.: 15/755,260

(22) PCT Filed: Aug. 29, 2016

(86) PCT No.: PCT/US2016/049185
§ 371 (c)(1),
(2) Date: Feb. 26, 2018

(87) PCT Pub. No.: WO2017/040366
PCT Pub. Date: Mar. 9, 2017

(65) Prior Publication Data
US 2018/0242971 A1    Aug. 30, 2018

Related U.S. Application Data

(60) Provisional application No. 62/211,198, filed on Aug. 28, 2015.

(51) Int. Cl.
*A61M 1/36*        (2006.01)
*A61F 2/06*        (2013.01)
*A61B 17/11*       (2006.01)

(52) U.S. Cl.
CPC ............. *A61B 17/11* (2013.01); *A61F 2/06* (2013.01); *A61M 1/3655* (2013.01);
(Continued)

(58) Field of Classification Search
CPC .............. A61M 1/3655; A61M 1/3659; A61M 2205/3334; A61M 2205/3331;
(Continued)

(56) References Cited

U.S. PATENT DOCUMENTS 4,141,060 A    2/1979  Lackore et al.
5,944,019 A *  8/1999  Knudson ............... A61B 17/11
                                              128/898
(Continued)

OTHER PUBLICATIONS

International Search Report of corresponding PCT/US2016/049185 dated Nov. 15, 2016.

*Primary Examiner* — Seema Mathew
(74) *Attorney, Agent, or Firm* — Dinsmore & Shohl LLP

(57) ABSTRACT

A vascular implant device configured to decrease turbulence in blood flow through an arteriovenous fistula is described. The implant includes an arterial section having a straight hollow tube, a venous section having a curved hollow tube divided into an orthogonal portion at the juncture of the arterial section, a curved portion, and a straight extension portion, and having a continual lumen and lumen surface. The curved portion curves approximately 90 degrees with respect to the arterial section, and the extension portion extends substantially parallel to the arterial section. A plurality of flow-conditioning tabs are located along the lumen surface in arrangements precisely designed to convert the turbulent blood flow that enters the venous section into substantially laminar flow, and to minimize oscillatory shear stress on the venous endothelium as the blood flow exits the device and enters the vein.

20 Claims, 13 Drawing Sheets

(52) U.S. Cl.
CPC ........... *A61B 2017/1107* (2013.01); *A61B 2017/1135* (2013.01); *A61F 2002/068* (2013.01); *A61F 2230/0023* (2013.01); *A61F 2230/0026* (2013.01); *A61F 2230/0043* (2013.01); *A61F 2240/002* (2013.01); *A61M 2206/11* (2013.01)

(58) Field of Classification Search
CPC .. A61M 1/101; A61M 39/227; A61M 1/1086; A61M 1/16; A61M 1/3663; A61M 2206/11; A61B 17/11; A61B 2017/1107; A61B 2017/1135; A61B 2017/1132; A61B 2017/1139; A61F 2/06
See application file for complete search history.

(56) References Cited

U.S. PATENT DOCUMENTS

| | | | |
|---|---|---|---|
| 6,605,053 B1 * | 8/2003 | Kamm | G16H 50/50 604/8 |
| 7,682,673 B2 * | 3/2010 | Houston | A61F 2/90 428/35.8 |
| 8,110,267 B2 | 2/2012 | Houston et al. | |
| 8,506,517 B2 | 8/2013 | Stergiopulos | |
| 9,561,320 B2 * | 2/2017 | Shields | A61M 1/3655 |
| 10,188,532 B2 * | 1/2019 | Houston | A61F 2/86 |
| 10,420,873 B2 * | 9/2019 | Shields | A61M 1/3655 |
| 2002/0049486 A1 * | 4/2002 | Knudson | A61B 17/11 623/1.1 |
| 2006/0184194 A1 * | 8/2006 | Pal | A61F 2/013 606/200 |
| 2007/0270939 A1 | 11/2007 | Hood et al. | |
| 2008/0140110 A1 * | 6/2008 | Spence | A61F 2/07 606/200 |
| 2011/0319976 A1 * | 12/2011 | Iyer | A61F 2/90 623/1.11 |
| 2012/0071965 A1 * | 3/2012 | Longo | A61B 17/11 623/1.35 |
| 2012/0130314 A1 | 5/2012 | Stonebridge et al. | |
| 2015/0119908 A1 | 4/2015 | Consigny et al. | |
| 2015/0182358 A1 | 7/2015 | Florescu | |
| 2015/0352273 A1 | 12/2015 | Shields et al. | |
| 2016/0113764 A1 * | 4/2016 | Sheahan | A61F 2/2418 623/2.17 |
| 2017/0049997 A1 * | 2/2017 | Chao | A61M 25/0097 |

* cited by examiner

ARTERIOVENOUS FISTULA IMPLANT EFFECTIVE FOR INDUCING LAMINAR BLOOD FLOW

PRIORITY CLAIM

This application claims priority to U.S. Provisional application No. 62/211,198, filed Aug. 28, 2015, the entire disclosure of which is incorporated herein.

TECHNICAL FIELD

Embodiments of the invention related to medical devices, and in particular provide a vascular implant designed to substantially convert turbulent blood flow into laminar flow in the setting of an arteriovenous fistula.

BACKGROUND

Dialysis vascular access provides a surgically created means of accessing the bloodstream and serves as a "lifeline" for greater than 2.6 million patients worldwide who rely on hemodialysis to treat their end-stage renal disease (ESRD). The three types of chronic vascular access for hemodialysis are native arteriovenous fistulas (AVFs), arteriovenous shunts using graft material, and tunneled double-lumen catheters. Of these, the AVF, created by surgically connecting an artery to a vein, is preferred for long-term hemodialysis/vascular access since it requires the fewest interventions of any type of access, and is associated with the lowest incidence of morbidity and mortality. The National Kidney Foundation Kidney Disease Quality Outcomes Initiative (NKF-KDOQI) clinical practice guidelines suggest a goal prevalence rate for native AVF of 65 percent. Despite this initiative, greater than 50% of AVFs fail to develop an adequate flow necessary for sustained clinical use. The primary reason most AVFs fail to "mature" is due to vessel narrowing in regions of the vessel were abnormal flow exists due to oscillatory flow separation and turbulence, and is characterized by venous stenosis and aggressive neointimal hyperplasia at the anastomotic region. These patients must then undergo numerous surgical procedures to promote AVF maturation, resulting in significant morbidity and an estimated cost of over $1 billion per year in the US. Despite the significance of this clinical problem, there are currently no effective therapies for improving AVF maturation.

Recently developed technologies focus on controlling the anatomical configuration of the AVF in order to improve hemodynamics, however large variability still exists. For example, the Optiflow™ Vascular Anastomotic System device manufactured and sold by Bioconnect Systems consists of a vascular conduit designed for a quick and controlled method for joining vessels. This technology emphasizes the importance of anatomical configuration on the resulting hemodynamics of the AVF; however does not address flow dynamics directly. Other solutions involve the use of synthetic grafts and stents to produce a helical blood flow pattern. Construction of an AVF implant creates conditions for increasing the flow of blood through the venous system. Fulfillment of these conditions reduces the risk of turbulence and endothelium injury, which, in turn, minimizes the potential for stenosis.

Clearly, there remains a compelling need in the art for quality chronic vascular access for hemodialysis suitable for repeated puncture and which permits a high blood flow rate for high-efficiency dialysis with minimal complications, with a minimal need for corrective interventions.

SUMMARY

Accordingly, embodiments of the invention provide a vascular implant configured to decrease turbulence and oscillatory flow patterns in blood flow through an arteriovenous fistula. The implant comprises a lumen comprising a plurality of flow-conditioning tabs positioned on an inner surface of the lumen in a configuration effective to reduce post-implant oscillatory shear stress on downstream venous endothelium and to substantially restore laminar flow by the time blood flow contacts venous endothelium.

According to one embodiment, an AVF implant is designed to optimize the blood flow before it contacts the venous endothelium, thereby substantially preventing the abnormal blood flow responsible for initiating AVF narrowing and subsequent maturation failure. Embodiments of the inventive device are intended to be implanted at the time of native AVF creation and to condition the turbulent flow into a laminar flow prior to exiting the device. By accomplishing this, the degree of AVF stenosis will be decreased and the rate of AVF maturation will be markedly improved.

One specific embodiment is directed to vascular implant devices configured to decrease turbulence in blood flow and substantially restore laminar blood flow through an arteriovenous fistula. The implants comprise: an arterial section comprising a straight hollow tube and having an arterial inlet end and an arterial outlet end and a port junction positioned between the inlet and outlet ends; a venous section comprising a hollow tube having a orthogonal portion of length L, a curved portion, and an extension portion having a venous outlet end, wherein the orthogonal portion joins and is flush with the port junction at an angle orthogonal to the arterial section, the elbow portion curves approximately 90 degrees with respect to the arterial section, and the extension portion extends substantially parallel to the arterial section for a length L'. The venous section comprises a continuous lumen surface and a plurality of flow-optimizing tabs located along the lumen surface.

According to one aspect, a plurality of blood flow conditioning tabs are located on the lumen surface of the implant, wherein each tab is a solid geometric form angled in the direction of blood flow, and wherein the distribution is configured to reduce turbulence in the blood flow by creating localized flow dynamics, such as counter-eddies, that act in opposition to the turbulence and oscillatory flow through the device. Tabs may be placed sequentially and/or circumferentially.

Another embodiment is directed to a method for minimizing turbulent and oscillatory blood flow through an artificially created arteriovenous fistula by implanting an embodiment of the inventive device into an AVF.

These and other embodiments and aspects of the invention will be more fully understood and clarified by reference to the Figures and Detailed Description below. The Figures are set forth to illustrate particular embodiments and should not be construed as limiting the scope of the invention as defined by the appended claims.

DETAILED DESCRIPTION

Figure 1A:
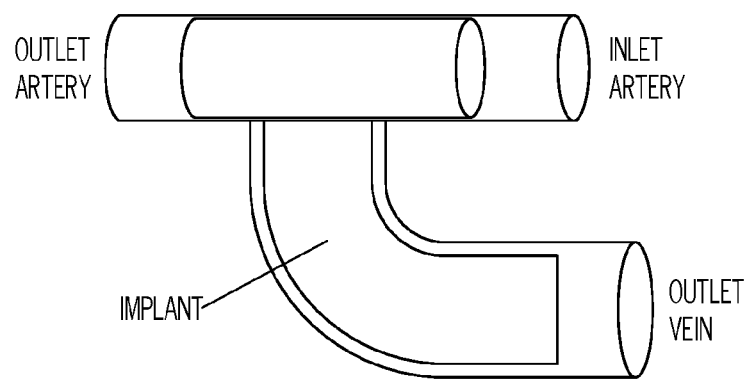
FIG. 1A) Schematic of AVF implant positioned within an AVF; 1B) Surgical photograph showing device positioned in side of an artery during AVF creation; 1C) Surgical photograph showing the device being inserted into the vein of the AVF and connection of the artery to the vein; 1D) Schematic depicting the flow of blood through the device and interior geometry which optimizes the flow profile at the venous outlet of the AVF.
Figure 1B:
Figure 1C:
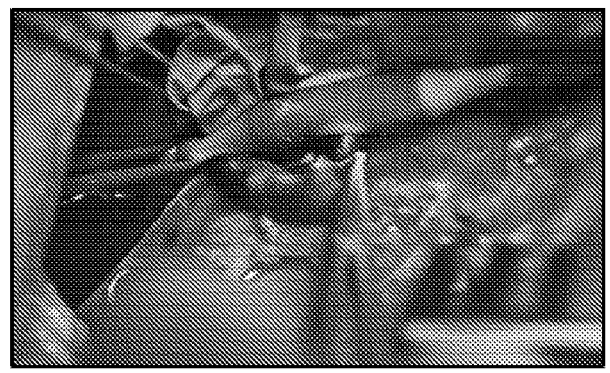
Figure 1D:
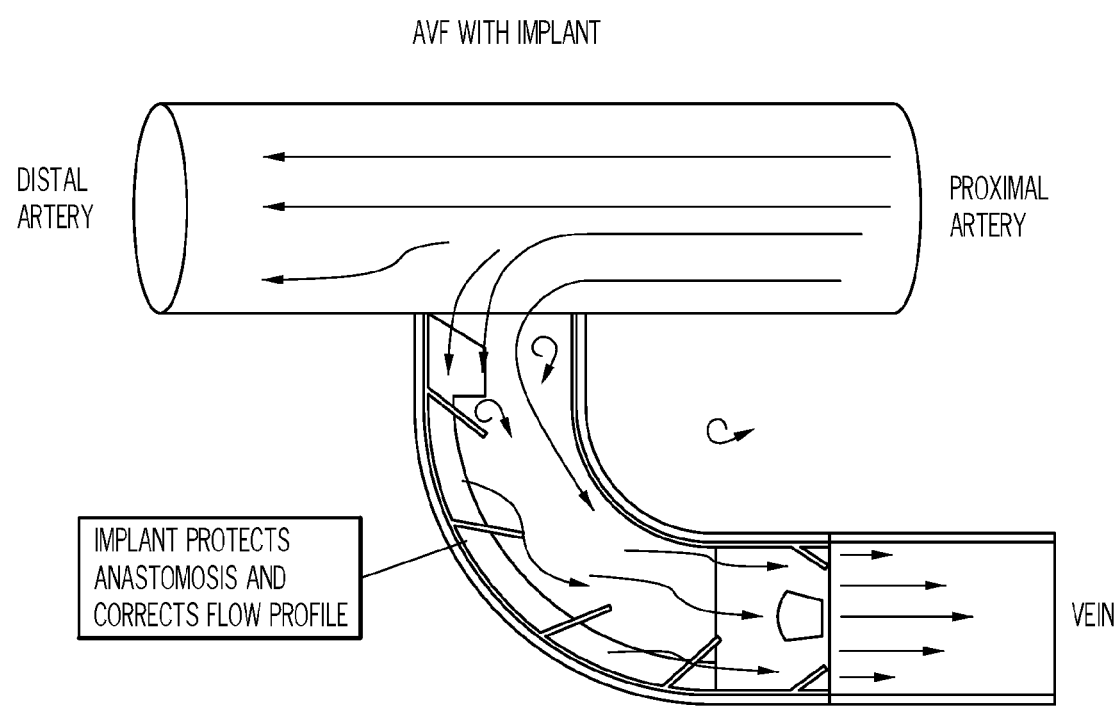
Figure 2:
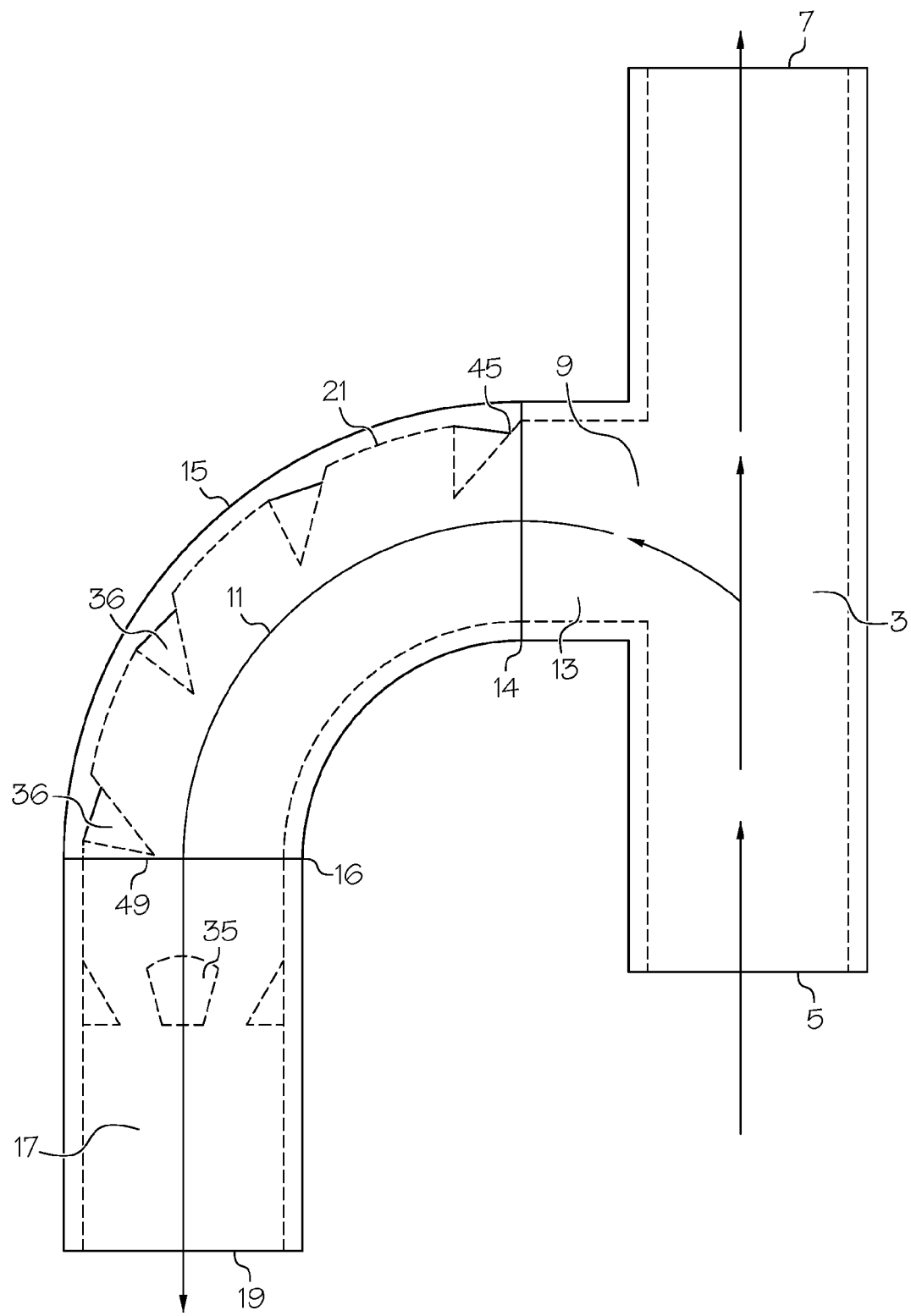
FIG. 2. Transverse section through an exemplary AVF device illustrating the overall shape and flow of blood through the device.

Endothelium lining the cardiovascular system is highly sensitive to hemodynamic shear stresses that act at the vessel luminal surface in the direction of blood flow. Physiological variations of shear stress regulate acute changes in vascular diameter and when sustained induce slow, adaptive, structural-wall remodeling. Shear stress is the force per unit area created when a tangential force (blood flow) acts on a surface (endothelium)—wherever flow occurs, shear stress exists. Regions of flow disturbances near arterial branches, bifurcations and curvatures result in complex spatiotemporal shear stresses. Changes in geometry resulting from creation of a native AVF result in uncompensated modification of shear stress at the endothelium.

Laminar flow is a well-ordered pattern of streamlined flow that occurs when a fluid flows in parallel layers, with friction between the successive layers. Oscillating flow includes any flow other than the bulk flow, and in normal vasculature occurs near the wall boundary and at bifurcations, bends, and valves; for example pulsatile flow, reciprocating flow, recirculation eddys, and reflux eddys are all forms of oscillating flow. Oscillatory shear stress is measured at a point in space by taking into account shear stresses that act in directions other than that of the bulk flow. Turbulent flow is chaotic flow in which the velocity at any given point varies continuously over time, even though the overall flow may be steady. In turbulent flow, the inertial force is more significant than viscous force and turbulent flow begins to be significant when the Reynolds number (flow velocity×fluid density×vessel diameter/fluid viscosity) exceeds a critical level. This critical Reynolds number becomes lower with an increase in complexity of vascular geometry. Turbulent blood flow is uncommon in normal circulation, but it occurs in human aorta at peak systole (especially during heavy exercise), and both turbulent flow and oscillatory flow are undesired consequences of AVF creation. The impact of the resultant oscillatory shear stress on the endothelium precipitates a cascade of adversely modulating EC signaling and gene expression, thus contributing to the development of vascular pathologies.

Embodiments of the invention provide a vascular implant designed to optimize blood flow through a blood vessel in the setting of an arteriovenous fistula. An AVF implant is inserted within an AVF at the anastomosis region where the artery is connected to the vein (FIG. 1). Specifically, the implant is inserted into the side of the artery orthogonal to the length of the vessel, and the vein is advanced over the opposite end to join the side of the artery. The implant allows blood to flow through the implant and exit through either the connected vein of the AVF or the downstream artery. Generally, the implant protects the anastomosis region of the AVF and optimizes blood flow through the AVF by a precisely constructed and configured series of small tabs located on the inner surface of the implant. These tabs redirect flow within the lumen of the implant and produce a substantially laminar/normal flow profile at the device outlet at the first contact with the venous endothelium.

According to a one embodiment depicted generally in FIG. 1 and by reference to FIG. 2 through FIG. 5, the device 1 consists of two thin-walled, hollow tubes that meet at an orthogonal angle. The two tubes roughly form a "J" shaped elbow with the arterial section 3 of the device being a straight hollow tube. A venous section 11 of the device comprises the curved portion 15 of the "J" shape and meets the straight, arterial end/port 9 at an orthogonal angle. At the port junction of the arterial and venous sections, the venous section 11, which is divided into three portions based on configuration, extends laterally as an orthongonal portion 13, followed by a 90 degree bend as the curved portion 15, and a straight outflow tract, or extension portion 16. Both the arterial and venous sections are hollow, allowing the passage of blood through the entire lumen of the device. Blood flows through an arterial inlet 5 and splits at the junction of the venous section 11. At this junction, blood continues to flow either through an arterial outlet 7 or through the venous section 11 of the device and out through the venous outlet 19. Within the venous section 11, blood flow is optimized by a series of tabs 23, 33, 35 located along the lumen in the curved portion and circumferentially at the juncture with the extension section.

One embodiment is directed to a vascular implant device 1 configured to decrease turbulence in blood flow through an arteriovenous fistula. The implant comprises: an arterial section 3 comprising a straight hollow tube and having an arterial inlet end 5 and an arterial outlet end 7 and a port junction 9 positioned between the arterial inlet 5 and arterial outlet 7 ends; a venous section 11 comprising a hollow tube having a orthogonal portion 13 of length L, a curved portion 15, and an extension portion 17 having a venous outlet 19 end, wherein the orthogonal portion 13 joins and is flush with the port junction 9 at an angle orthogonal to the arterial section 3, the curved portion 15 curves approximately 90 degrees with respect to the arterial section 3, and the extension portion 17 extends substantially parallel to the arterial section 3 for a length L', said venous section 11 further comprising a continuous lumen surface 21; and a plurality of flow-optimizing tabs 23 located along the lumen surface 21.

Figure 3:
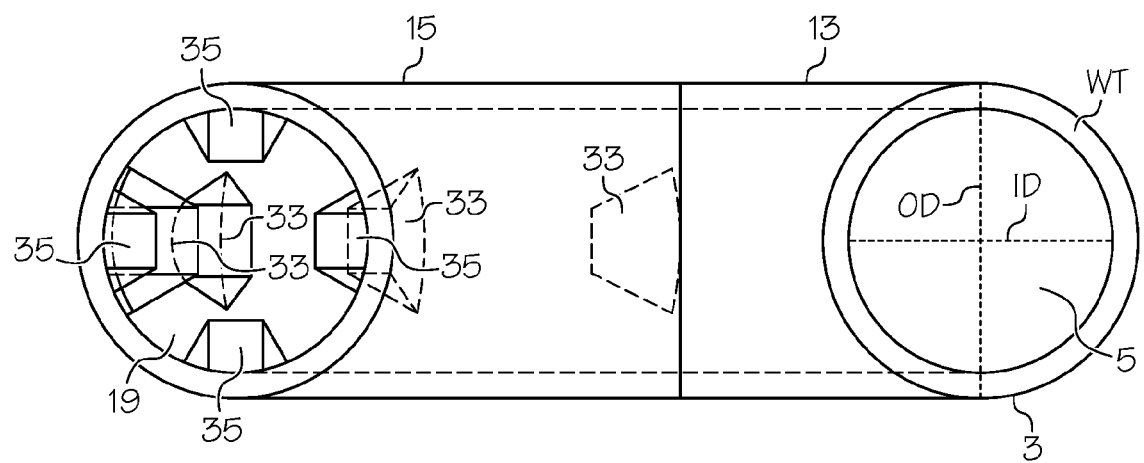
FIG. 3 Side section of an exemplary embodiment of the device showing the lumens of the arterial and venous sections with their equal inner diameters (ID), outer diameters (OD), and wall thickness (WT).
Figure 4:
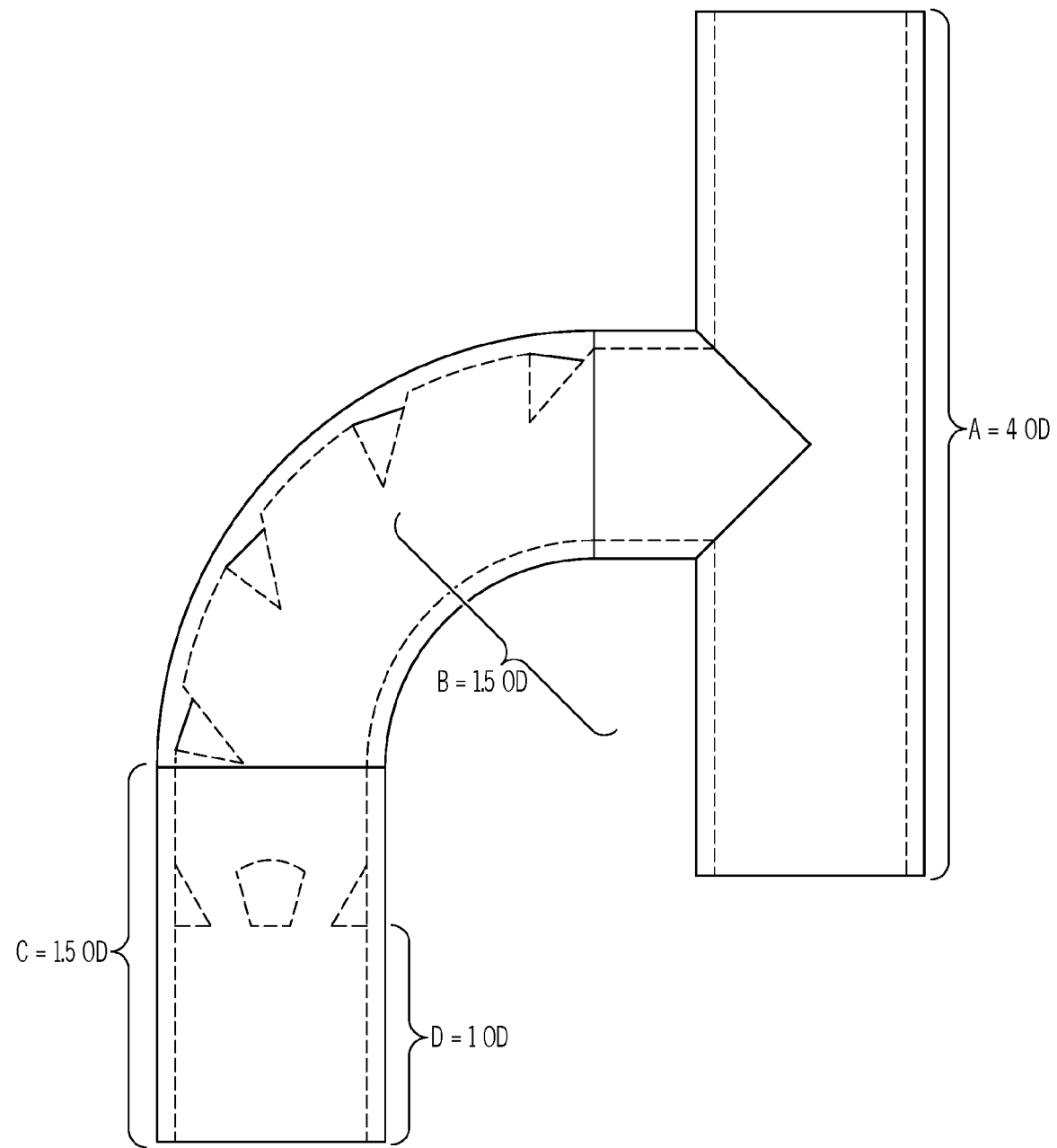
FIG. 4 Transverse section of an exemplary embodiment of the device describing optimized lengths of each element compared the outer diameter (OD) of the device, including the length of the arterial section which is placed in the side of the artery, the radius of curvature for 90 degree elbow of the venous section, the length of the straight outflow tract of the venous section, the ideal distance between the venous outlet and the end of the flow optimizing tabs located in outflow tract.
Figure 5:
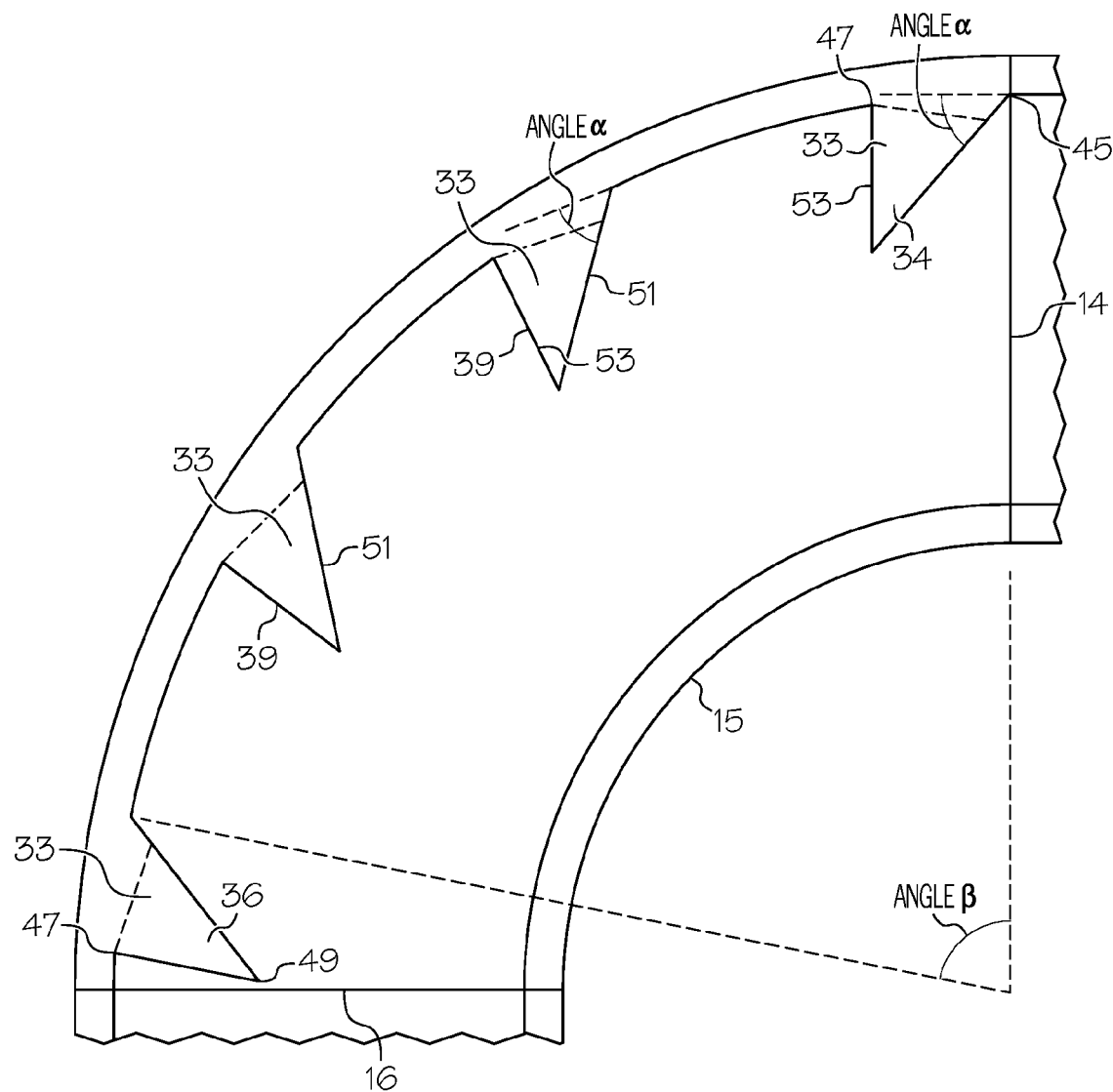
FIG. 5 Transverse section through the curved portion of the venous section showing detailed geometry of an exemplary sequential set of 4 flow optimizing tabs.
Figure 6A:
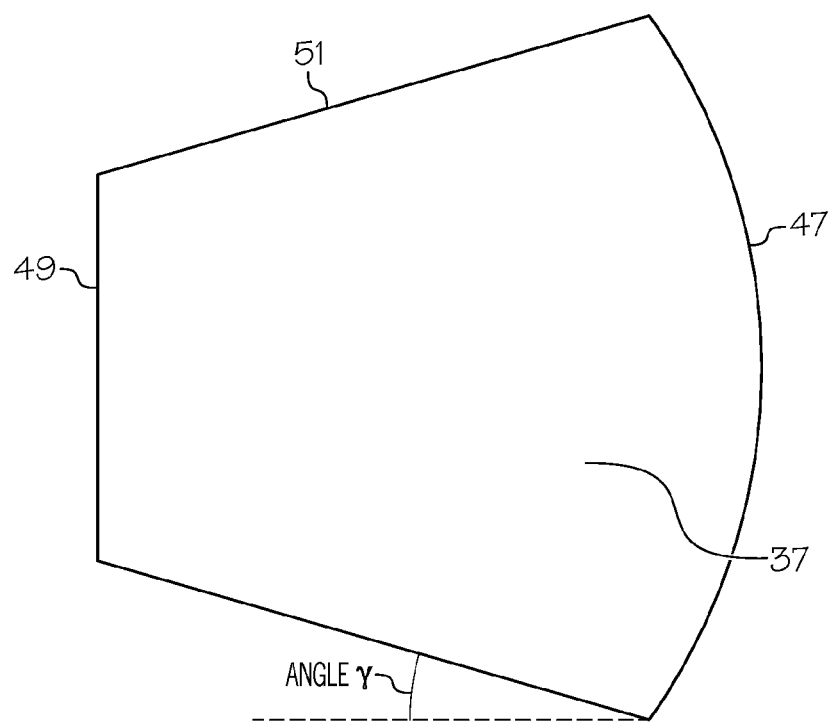
FIG. 6A Lateral view of the flow optimizing tabs located within the venous section of the device; 6B) isometric view of a flow-optimizing tab; The base of each tab protrudes inward from the wall of the device at an acute angle ($\propto$) to a normal to the lumen surface; the top and bottom of each tab are chamfered at an acute angle ($\gamma$), creating a tab whose top edge has a shorter length than its leading base edge.
Figure 6B:
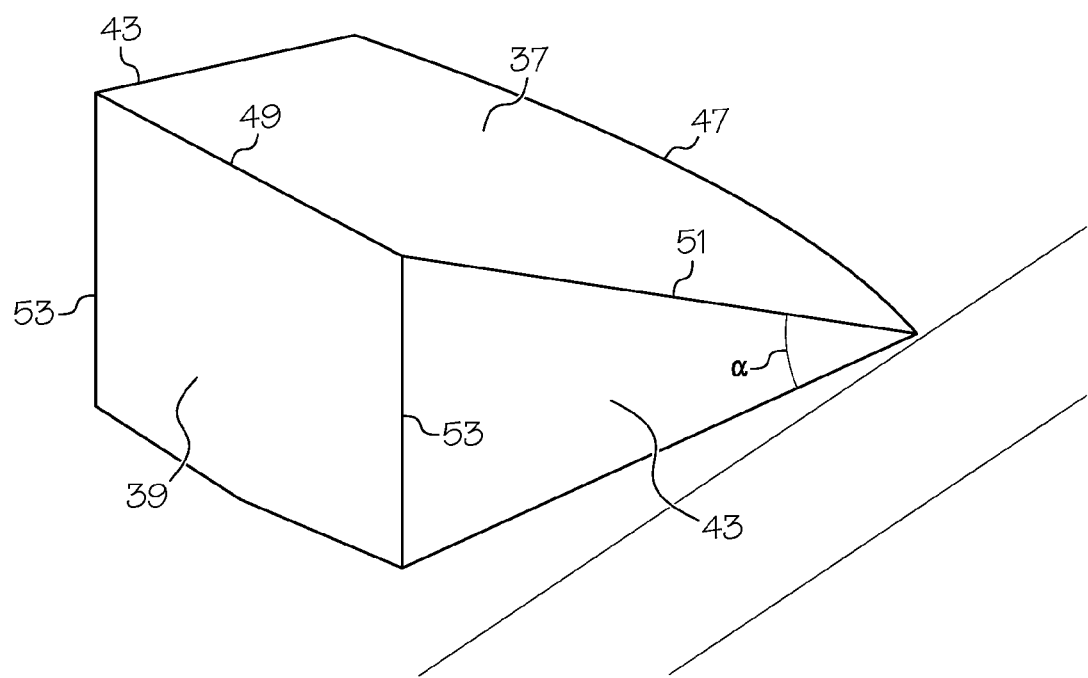

According to some embodiments, the venous 11 and arterial sections 3 of the device have the same inner and outer diameters (ID and OD), and wall thickness, WT (FIG. 3 and FIG. 4). The outer diameter is designed to be equal to the inner diameters of the arterial and venous vessels in which the device is to be implanted; thereby forcing all blood to flow through the lumen of the implant and not between the implant and the inner lining of the blood vessels. At the junction of the arterial and venous sections, the first orthogonal part of the venous section ideally extends for a length of 1 OD before the 90 degree bend begins. This distance allows ample room between the venous outlet 19 and arterial inlet 5 in order for the vein to be pulled over the venous outlet 19 and advanced up to the port junction 9. Once the vein is advanced up to the arterial section 3, the end of the vein can be sutured to the side of the artery.

According to specific embodiments, the arterial section 3 and the venous section 11 have an inner diameter 25 of length ID and an outer diameter 27 of length OD and a wall thickness 29 WD. The OD is substantially equal to an inner diameter of the vasculature 31 into which the device is to be implanted. According to very specific embodiments, L is equal to at least 1×OD. According to very specific embodiments, the arterial section 3 comprises a length measuring at least 4×OD. According to other specific embodiments, the curved portion 15 comprises a radius of curvature 16 measuring at least 1.5×OD and L' is equal to at least 1.5 OD.

In other specific embodiments, the plurality of flow-optimizing tabs 23 comprises one sequential set 33 of greater than one tabs equally spaced along the outer lumen surface 21 of the curved portion 15, and one circumferential set 35 of greater than one tabs equally spaced in the lumen surface 21 of the extension portion 17, all tabs being angled inward toward the venous outlet 19. According to more specific embodiments, the sequential set 33 comprises at least 4 tabs and the circumferential set 35 comprises at least 4 tabs. In very specific embodiments, the sequential set consists of 4 tabs and the circumferential set consists of 4 tabs. In some very specific embodiments, the set of circumferential tabs 35 is located in the extension portion 17 a distance measuring at least one OD from the venous outlet 19. According to specific embodiments, both sets of tabs are equally spaced along the outer wall of the curved portion 15 and inner diameter of the extension section 17, respectfully. These tabs are angled inward and toward the venous outlet 19 of the device.

Although the tab aspect of the inventive device is described with specificity, it will be clear to a person of ordinary skill in the art that certain parameters may co-vary with retention of the desired function. Such co-variance is within the skill of an ordinary practitioner. In specific embodiments, each tab 23 is a solid geometric form comprising five surfaces: a leading surface 37, a trailing surface 39, a base 41, and two triangular surfaces 43, a leading edge 45 at the intersection of the base and the leading surface, a trailing edge 47 at the intersection of the base and the trailing surface, and a top edge 49 at the intersection of the leading surface and the trailing surface. In some specific embodiments the trailing edge 47 has a length substantially equal to the length of the top edge 49 and shorter than the length of the leading edge 45. The direction of blood flow is from the leading edge 45 toward the trailing edge 47.

According to some specific embodiments, the set of sequential tabs 33 is further defined as comprising a first tab 34 and a last tab 36. The first tab is the first tab reached by blood flow entering the venous section 11. The leading edge 45 of the first tab 34 is located at a juncture 14 between the orthogonal portion 13 and curved portion 15, and the top edge 49 of the last tab 36 is located at a juncture 16 between the curved portion 15 and the extension portion 17. Such positioning optimizes the flow-conditioning; however it is contemplated that deviations from this positioning that also improve blood flow-conditioning are within the scope thereof.

In specific embodiments, the two triangular surfaces 43 are congruent right triangles, and each hypotenuse 51 corresponds to a side edge of the leading surface 37, and each orthogonal leg 53 corresponds to a side edge of the trailing surface 39. The terms leading and trailing are adopted herein to reflect which surface/edge the blood flow encounters first as it transits the device, with "leading" denoting the first-encountered. In very specific embodiments, the angle between the leading surface 37 and the base 41, (the angle opposite the trailing surface 49 in some embodiments) is α, and α is acute. In more specific embodiments, α is between 30° and 50°.

According to specific embodiments, the trailing surface 39 is substantially rectangular and is oriented normal to a tangent at a point on the curved portion, has a height measuring H, and H is equal to between 0.25 and 0.4 times ID. According to some specific embodiments, the leading edge 45 has a length measuring at least ⅓ ID, the top edge 49 has a length, and a ratio of the length of the top edge 49 to the length of the leading edge 45 is between 0.25 and 0.5. According to very specific embodiments, the distance each tab protrudes into the lumen is between 0.25 and 0.4 times the ID of the lumen. It is not necessary that ever tab be the same size; although in very specific optimized embodiments all tabs are substantially the same size. In other very specific embodiments the tabs are equally spaced over an angle less than 90 degrees (angle β) such that the tip of the last tab is congruent with the end of the 90 degree curvature of the curved portion. Furthermore, each tab may be chamfered at an acute angle from the leading edge to the top edge of the tab as its projects upward and inward (Angle γ).

Embodiments of the implant may be fabricated to be solid and non-porous and may be manufactured from any suitable biocompatible polymer. Biocompatible polymers are well known in the vascular arts, for example, as disclosed in Chauvel-Lebret, Dominique et al. "Biocompatibility of Elastomers." *Polymeric Biomaterials*. Boca Raton, Fla.: CRC, 2013. 415-93; Gourlay, Terence et al. "Vascular Implants for Peripheral Arterial Bypass and Aortic Aneurysm Repair." *Biomaterials and Devices for the Circulatory System*. Oxford: Woodhead Pub., (2010) 217-29; and Malhotra, Ashim, "Improving Matters of the Heart: The Use of Select Pharmaceutical Polymers in Cardiovascular Intervention." *Handbook of Polymers for Pharmaceutical Technologies: Structure and Chemistry*. Vol. 1. Scrivener LLC, 2015. 351-67, the entire disclosures of which are incorporated herein by reference. According to specific embodiments, the biocompatible polymer is selected from one or more of polylactic acid, poly(lactic-co-glycolic) acid, poly(caprolactone), and polysiloxane.

The implanted may be coated, for example, with coatings fabricated to inhibit cell adhesion, immune reactions, and thrombosis, as are well-known in the art. (See, for example, Frost, M. C. et al. (2005). Polymers incorporating nitric oxide releasing/generating substances for improved biocompatibility of blood-contacting medical devices. *Biomaterials*, 26(14), 1685-93; Rudolph, A. et al. (2015). Surface Modification of Biodegradable Polymers towards Better Biocompatibility and Lower Thrombogenicity. *PloS One*, 10(12), e0142075; Taubert, Andreas et al. "Surface Modification of Polymeric Biomaterials" *Biomaterials Surface Science*, Wiley-VCH Verlag GmbH, 2013. 89-158; and Vladkova, Todorka G. et al. "Surface Engineering of Blood Contacting Polymeric Biomaterials" *Surface Engineering of Polymeric Biomaterials*. 231-93, the entire disclosures of which are incorporated herein by this reference. At least a portion of the implant may be fabricated from a biodegradable material. According to some embodiments, the biodegradable material biodegrades in a time frame sufficient for the AVF vein to arterialize. Generally, however, embodiments of the inventive implant are designed for chronic use and to sustain the mechanical and physiological demands of chronic use. The implant may be fabricated from a polymer, such as a silicone polymer, comprising drug-eluting technology allowing it to release anti-thrombotic, anti-proliferative, or other types of medications over time.

Further, as an implant, the dimensions and parameters of the device may be manufactured as patient-specific. In some embodiment, the device is fabricated from a computer-assisted three-dimensional printing protocol comprising patient-specific geometry. Such technologies are well known in the art (See, for example, He, Y. et al. (2014). Fabrication of low cost soft tissue prostheses with the desktop 3D printer. *Scientific Reports*, 4, 6973; Marro, A. et al. Three-Dimensional Printing and Medical Imaging: A Review of the Methods and Applications. *Current Problems in Diagnostic Radiology*, 45(1), 2-9; and O'Neill, B. et al. (2015) Transcatheter caval valve implantation using multimodality imaging: roles of TEE, CT, and 3D printing. *JACC. Cardiovascular Imaging*, 8(2), 221-5, the entire disclosures of which are incorporated herein.

Other embodiments are directed to methods for minimizing turbulent flow through an artificially created arteriovenous fistula. The methods comprise implanting an inventive embodiment of the device as disclosed herein in a subject in need thereof. In specific embodiments, the subject is in need of hemodialysis, and in very specific embodiments, the subject is in chronic need of hemodialysis. Minimizing turbulent flow comprises one or more of inducing counter-rotating vortices in the blood flow and reducing oscillatory shear on the venous endothelium, or some combination thereof.

Broadly, embodiments of the implant are configured to condition blood flow though an AVF by decreasing turbulence in the blood flow and oscillatory shear stress on the venous endothelium. The implant comprises a lumen comprising a plurality of flow-conditioning tabs positioned on an inner surface of the lumen in a configuration effective to reduce post-implant oscillatory shear stress on downstream venous endothelium and to substantially restore laminar flow by the time blood flow contacts venous endothelium. The tabs may be oriented in a variety of configurations effective to reduce turbulence and configurations optimized for minimization of turbulence are set forth specifically herein.

Figure 7:
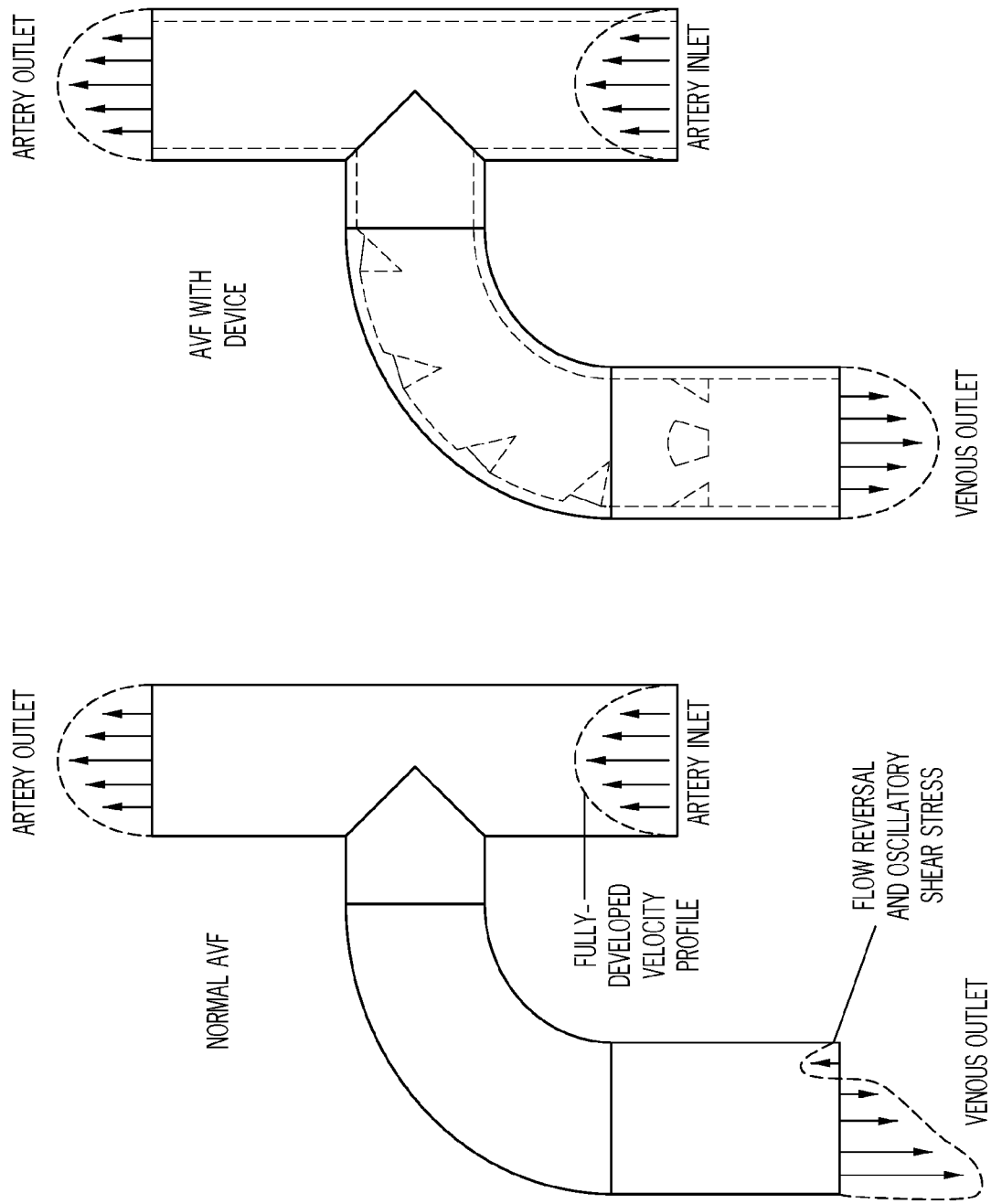
FIG. 7 Schematic illustrating comparing a typical velocity profile within a native AVF and an AVF with the disclosed device. In native fistula (left), the arterial inlet and outlet velocity profiles are typically parabolic, characteristic of fully-developed flow. The venous outlet of native AVF, however, is characterized by regions of flow separation and flow reversal along the inner wall of the vein, predisposing this region to neointimal hyperplasia formation and subsequent vessel narrowing. In contrast, the AVF implanted with an embodiment of the device restores a nearly fully-developed velocity profile at its outlet. This reduces the risk of neointimal hyperplasia formation and AVF narrowing.

Within a typical AVF, the blood flow entering the artery of the fistula has a fully-developed velocity profile with a parabolic shape in cross-section (FIG. 7). This type of flow is characterized by a velocity which is greatest at the center of the vessel and approaches zero at the vessel wall. As blood enters the vein of the AVF, the blood flows toward the outer wall of the vein and downstream vessel. This separation of flow causes flow reversal and oscillatory shear stress along the inner wall of the vein (FIG. 7). This oscillatory shear stress and flow reversal have been identified as a key factors instigating neointimal hyperplasia formation and vessel narrowing, which lead to AVF maturation failure. As has been shown under fluid flow conditions, implanting embodiments of the device results in a nearly fully-developed velocity profile that resembles normal physiological flow at the venous outlet that is maintained as the blood travels downstream (FIG. 7). By maintaining a normal velocity flow profile across the vessel, the incidence of AVF narrowing is reduced.

Figure 8:
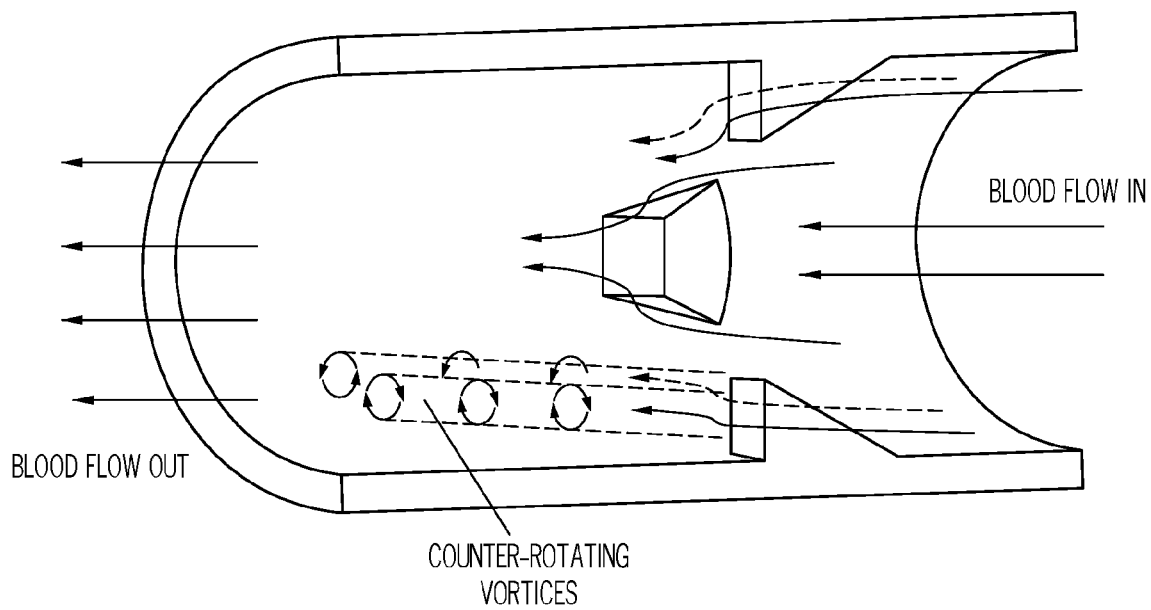
FIG. 8 Cut-away section of an embodiment of the device showing the flow of blood around the tab array and generation of counter-rotating vortices. Blood flow through the device is depicted by streamline arrows. Dashed arrows indicate blood flow behind the opposing side of the tab. The bottom tab exemplifies a pair of counter-rotating vortices created by each tab. These vortices redistribute any asymmetries in the velocity profile by promoting the exchange of energy between regions of high and low velocity. However, these vortices quickly dissipate due to their close proximity to the device wall, producing a nearly-fully developed flow at the device outlet.

Without wishing to be bound by theory, the present investigators posit that the inventive devices improve AVF maturation and function primarily by performing 2 roles. First, the placement of the device within the lumen of the AVF serves to protect the adjacent vessel wall where the artery and vein are connected. The solid, non-porous wall prevents the migration of the vessel wall into the lumen of the device and also provides structural support preventing AVF collapse. Second, blood flow is conditioned and optimized as it passes through the AVF such that the flow exhibits a substantially physiologically normal velocity profile at the venous outlet. This latter function is achieved by the placement of the blood flow conditioning and optimizing tabs located along either the venous curve, the extension section, or both. As blood flow reaches the tabs, the blood is forced to flow between and around the tabs. As blood flow is deflected off the leading face (depicted as trapezoidal) of each tab positioned along the lumen surface along the outer curve of the curved portion, it is redistributed toward the inner side of the curve. This deflection causes an increase in pressure at the trailing end of the tab compared to the sides and leading end. This difference in pressure causes blood to flow outward around the sides and tips of the tabs as illustrated by the flow lines in FIG. 8. This flow around each side of a tab causes the formation of counter-rotating vortices which originate at the top edge of each tab (FIG. 8). The counter-rotating vortices flow downstream and very quickly exchange momentum between the flow at the center of the lumen and the flow at the wall. These vortices quickly migrate to the wall in the wake of the tabs and decrease in intensity due to high shear stress at the device wall.

By combining tabs into a series, circumferential, or composite arrangement, a vigorous cross stream mixing is achieved which rapidly mixes faster velocity regions with slower regions. After passing through both sets of flow optimizing tabs in accordance with specific embodiments of the invention, a nearly fully-developed velocity profile is achieved at the venous/device outlet.

EXAMPLE

Figure 9:
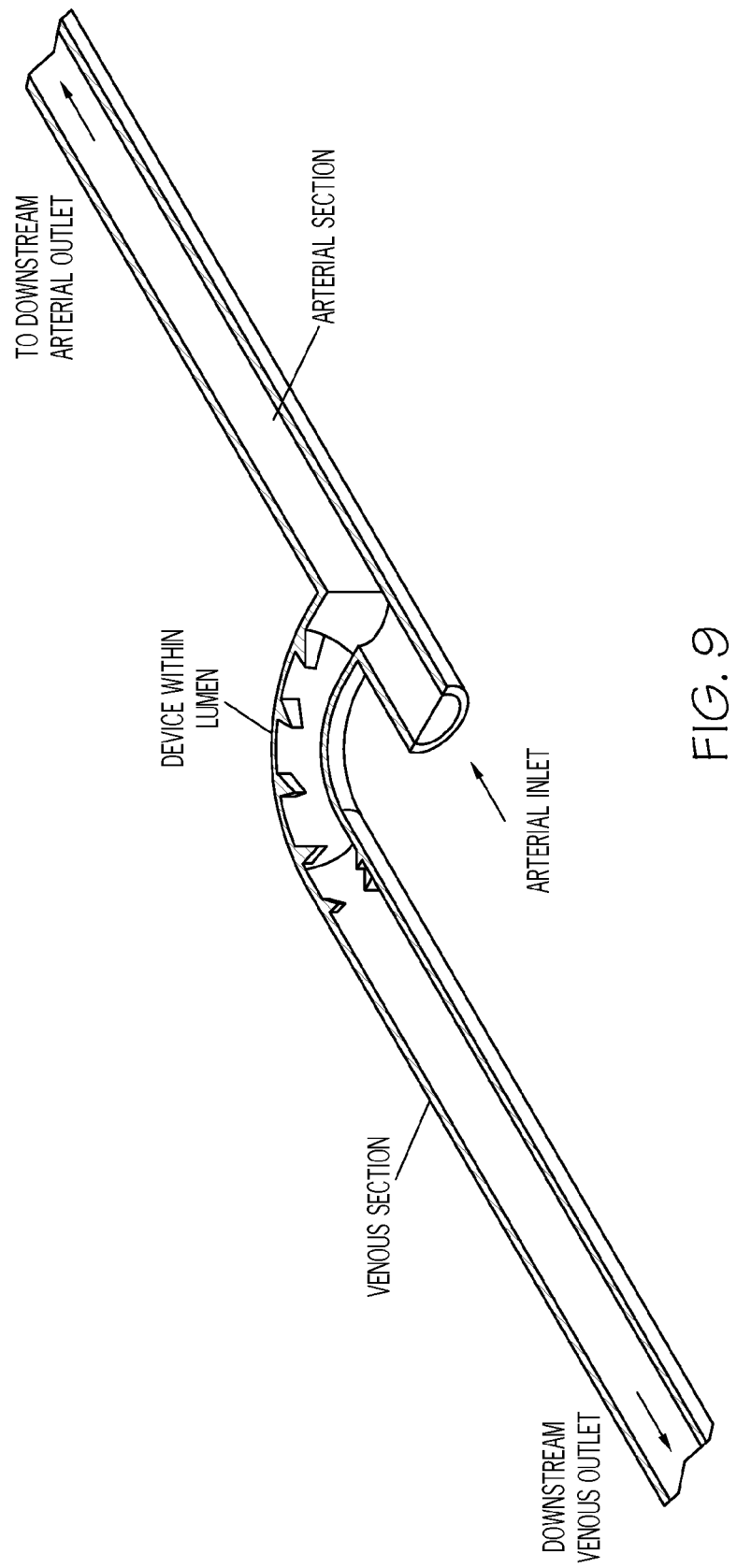
FIG. 9 Sets forth a three dimensional model used for CFD analyses of the disclosed device. The device shown was placed within the side of the red tube to mimic the artery of an AVF. The connecting vein was attached to the venous outlet of the device. The lengths of the downstream artery and vein tubes were 15 times the inner diameter of the tube to allow sufficient distance for flow disturbances to dissipate.

Solidworks™, a commercially available three-dimensional computer-aided design (CAD) software with integrated computational fluid dynamic (CFD) capabilities, was utilized for the following study. CFD analyses were conducted in three dimensional models in which the disclosed device was placed in the side of a 6 mm tube to represent the artery portion of the AVF. Similarly, a venous tube was inserted over the venous end of the device (FIG. 9). A model without the device was also constructed to represent a native AVF. The venous and arterial outlets were placed 15-pipe diameters downstream of the device's trailing edges such that the impact of the device could be documented as a function of downstream distance. The computational domain generated for the model consisted of approximately 1.2 million Cartesian fluid cells. Numerical simulations were performed using the Flow Simulation package within the Solidworks™ software.

The Solidworks™ Flow Simulation CFD package was utilized to calculate the three-dimensional, incompressible, non-Newtonian blood flow through the AVF and the device. An implicit time integration scheme was used to solve the time-dependent Navier-Stokes equations, assuming a cardiac cycle period of 1 second. Three complete flow cycles were solved in order to damp the initial transients of the fluid. For boundary conditions, a pulsatile fully developed parabolic velocity profile was prescribed at the arterial inlet and outlet (FIG. 9). At the venous outlet, a pulsatile venous blood pressure boundary condition was applied as measured in a native AVF. All walls were assumed rigid, and a no-slip boundary condition was applied at the walls (i.e. zero velocity). To mimic the non-newtonian nature of blood, the Carreau viscosity model was imposed. A detailed descriptions of the solvers employed in the Solidworks™ Flow Simulation package are available from Dassault Systems, Inc., the developer of Solidworks™ 2015.

Figure 10:
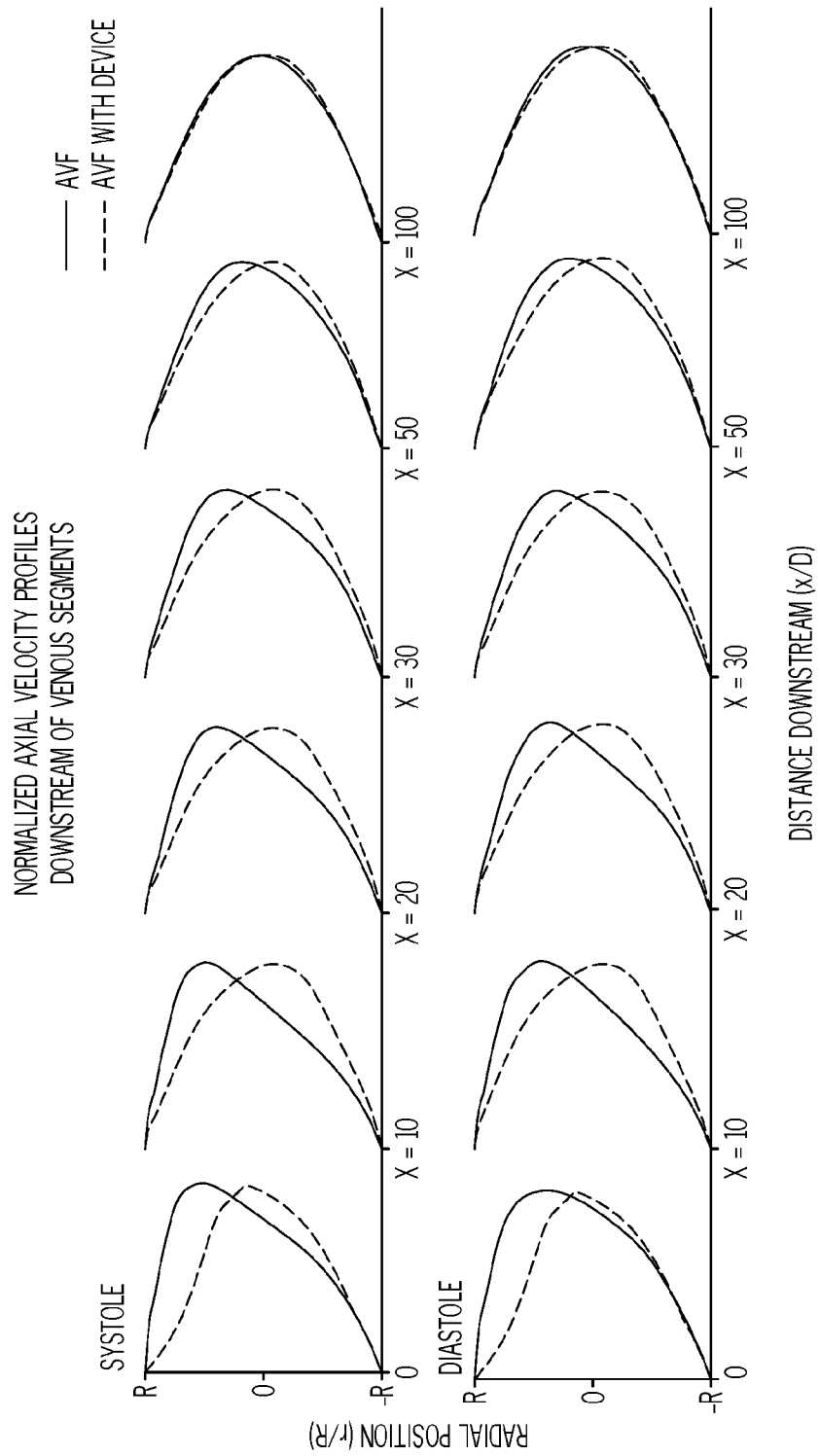
FIG. 10 Graphs shows a comparison of axial velocity profiles between modeled AVFs with and without the disclosed device. Axial velocity profiles are shown at multiple distances downstream of the device outlet during the systolic phase of heart contraction. For each set of curves, the maximum velocity is located at the peak of each curve, and a velocity of zero is present at the ends of each curve. The distribution of this velocity across the lumen of the vessel is described by the left axis, with zero representing the center of the lumen and R and –R representing the outer and inner walls, respectfully. Distances downstream are measured as the number of vessel diameters. Axial velocity profiles are shown at multiple distances downstream of the device outlet during the diastolic phase of heart relaxation.

These analyses compared axial velocity profiles of the native AVF and AVF with the device at multiple locations downstream of the device's venous outlet. FIG. 10 shows the differences in the axial velocity profiles between the two configurations at the peak of systole (when the heart is contracted) and diastole (when the heart is relaxed). It can be seen that during both phases of the cardiac cycle the native AVF has a velocity profile that is not symmetric and is shifted toward the outer wall of the vessel. Furthermore, in the native AVF, a full ten diameters of vessel length (X=10 OD) is required to restore the normal parabolic flow profile typical of fully-developed flow. In contrast, the AVF with the disclosed device has a velocity profile that is nearly parabolic at the exit of the device (X=0 OD) during both systole and diastole.

Deviation from fully-developed flow was also determined for each AVF configuration by assessing the coefficient of variance (CoV) of the velocity at each distance downstream of the device outlet. For comparison, a fully developed velocity profile was estimated using the empirical power-law equation:

$$\frac{v}{v_{max}} = \left(\frac{y}{R}\right)^{\frac{1}{n}} \text{ where } n = 1.7 + 1.8 \log Re$$

Figure 11:
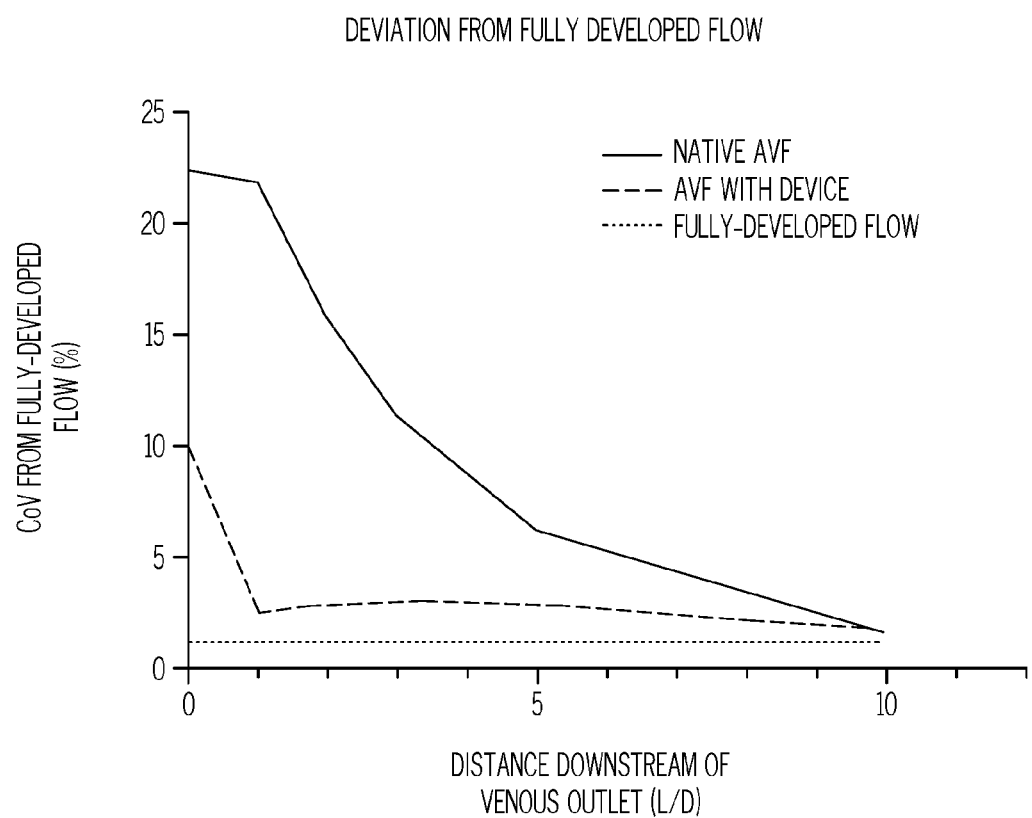
FIG. 11 Graphical illustration of deviation of each AVF configuration from a fully developed velocity profile at multiple locations downstream of the device outlet. For each AVF configuration, systolic velocity profiles at multiple locations downstream of the device outlet location were compared to a fully-developed flow profile (dotted line) and used to compute the coefficient of variation. As blood exits the device and flows downstream the deviation from the ideal profile decreases to a point where the blood flow resembles fully-developed flow. For the native AVF configuration this occurs at a distance around 10 diameters downstream (solid line). After implanting the disclosed device, this distance is decreased to approximately 1 diameter downstream of the device outlet (dashed line).

V is the velocity at a given distance across the diameter of the lumen, Vmax is the largest velocity across the lumen, y is the distance from the point in the center of the lumen to the wall, R is the radius, and Re is the Reynolds number. This equation is only an approximation of a fully developed flow profile and was found to deviate from an actual fully developed profile by approximately 0.89% at the Reynolds number of 780. For each distance downstream, the deviation between the estimated fully-developed velocity profile and the computed AVF profile was used to compute the coefficient of variation. FIG. 11 shows how each AVF configuration compares to the fully-developed profile at each distance downstream during systole. As can be seen, the native AVF greatly deviates from the ideal fully-developed flow at the location of the device outlet (L/D=0), and a downstream distance of 10 diameters is needed to order to develop a velocity profile which resembles fully-developed flow. In contrast, the AVF with the device has less than half the deviation of the native AVF at the device outlet, and only a distance of 1 diameter (6 mm) is required to achieve a stable velocity profile with only a 2.5% deviation from fully-developed flow.

Although certain aspects and features of the inventive device have been described herein with particularity and specificity, a person of ordinary skill in the art will readily comprehend that various arrangements and parameters may be employed while remaining with the scope of the claims, as appended hereto.

The invention claimed is:
1. A vascular implant device configured to decrease turbulence in blood flow through an arteriovenous fistula, the implant comprising:
   an arterial section comprising a straight hollow tube and having an arterial inlet end and an arterial outlet end and a port positioned between the inlet and outlet ends;

a venous section comprising a hollow tube having a orthogonal portion of length L, a curved portion, and an extension portion having a venous outlet end, wherein the orthogonal portion joins and is flush with the port at an angle orthogonal to the arterial section, the curved portion curves approximately 90 degrees with respect to the arterial section, and the extension portion extends substantially parallel to the arterial section for a length L', said venous section further comprising a continuous lumen surface; and a plurality of flow-conditioning tabs located along the lumen surface, wherein the arterial section and the venous section have an inner diameter of length ID and an outer diameter of length OD and a wall thickness WD, said OD being substantially equal to an inner diameter of the vasculature into which the device is to be implanted.

2. The vascular implant according to claim 1, wherein L is equal to at least 1×OD.

3. The vascular implant according to claim 2, wherein the plurality of flow-conditioning tabs comprises one sequential set comprising at least 2 tabs equally spaced along the lumen surface of an exterior curve of the curved portion and one circumferential set comprising at least 2 tabs equally spaced on the lumen surface of the extension portion, all tabs being angled inward toward the venous outlet.

4. The vascular implant according to claim 3, wherein the sequential set comprises at least 4 tabs and the circumferential set comprises at least 4 tabs.

5. The vascular implant according to claim 3, wherein the set of circumferential tabs is located in the extension portion a distance measuring at least 1×OD from the venous outlet.

6. The vascular implant according to claim 3, wherein each tab is a solid geometric form comprising: five surfaces: a leading surface, a trailing surface, a base, and two triangular surfaces; a leading edge at the intersection of the base and the leading surface, a trailing edge at the intersection of the base and the trailing surface, and a top edge at the intersection of the leading surface and the trailing surface, said trailing edge having a length substantially equal to the length of the top edge and shorter than the length of the leading edge, wherein the direction of blood flow defined as from the leading edge toward the trailing edge.

7. The vascular implant according to claim 6, wherein the set of sequential tabs comprises a first tab and a last tab, further wherein the leading edge of the first tab is located at a juncture between the orthogonal portion and curved portion, and the top edge of the last tab is located at a juncture between the curved portion and the extension portion.

8. The vascular implant according to claim 6, wherein the two triangular surfaces are congruent right triangles and each hypotenuse corresponds to a side edge of the leading surface, and each orthogonal leg corresponds to a side edge of the trailing surface.

9. The vascular implant according to claim 6 wherein the angle between the leading surface and the base is α, and α is between 30° and 50°.

10. The vascular implant according to claim 6, wherein the trailing surface has a height measuring H, and H is equal to between 0.25 and 0.4×ID.

11. The vascular implant according to claim 6, wherein the leading edge has a length measuring at least ⅓ ID, the top edge has a length, and a ratio of the length of the top edge to the length of the leading edge is between 0.25 and 0.5.

12. The vascular implant according to claim 1 wherein the arterial section comprises a length measuring at least 4×OD.

13. The vascular implant according to claim 1, wherein the curved portion comprises a radius of curvature measuring at least 1.5×OD, and L' is equal to at least 1.5 OD.

14. The vascular implant according to claim 1, wherein the vascular implant is fabricated from a solid, non-porous biocompatible polymer.

15. The vascular implant according to claim 14, wherein the biocompatible polymer is selected from a polylactic acid, a poly(lactic-co-glycolic) acid, a poly(caprolactone), and a polysiloxane.

16. The vascular implant according to claim 14, wherein the device is fabricated from a computer-assisted three-dimensional printing protocol comprising patient-specific geometry.

17. A method for decreasing turbulent blood flow through an artificially created arteriovenous fistula, the method comprising implanting the device according to claim 1.

18. The method according to claim 17, wherein decreasing is effectuated by inducing counter-rotating vortices in the blood flow, reducing oscillatory flow, or some combination thereof.

19. A vascular implant configured to decrease turbulence in blood flow through an arteriovenous fistula, the implant comprising an arterial section comprising a straight hollow tube and having an arterial inlet end and an arterial outlet end and a port positioned between the inlet and outlet ends;

a venous section comprising a hollow tube flush with the port at an angle orthogonal to the arterial section, said venous section further comprising a continuous lumen surface, said continuous lumen surface comprising a plurality of flow-conditioning tabs positioned in a configuration effective to induce counter-rotating vortices in the blood flow which substantially dissipate prior to the blood flow exiting the implant, wherein the arterial section and the venous section have an inner diameter of length ID and an outer diameter of length OD and a wall thickness WD, said OD being substantially equal to an inner diameter of the vasculature into which the device is to be implanted.

20. The vascular implant according to claim 19, wherein the plurality of tabs are positioned sequentially along a section of the lumen, or circumferentially along an inner diameter of the lumen, or some combination thereof.

* * * * *